US00PP27375P3

(12) United States Plant Patent
Robacker et al.

(10) Patent No.: US PP27,375 P3
(45) Date of Patent: Nov. 15, 2016

(54) ***VITEX AGNUS-CASTUS* PLANT NAMED 'V0502-33'**

(50) Latin Name: *Vitex agnus-castus*
Varietal Denomination: V0502-33

(71) Applicant: University of Georgia Research Foundation, Inc., Athens, GA (US)

(72) Inventors: Carol D. Robacker, Peachtree City, GA (US); Amanda J. Hershberger, San Jose, CA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 97 days.

(21) Appl. No.: 14/544,010

(22) Filed: Nov. 12, 2014

(65) Prior Publication Data

US 2016/0135349 P1 May 12, 2016

(51) Int. Cl.
*A01H 5/02* (2006.01)

(52) U.S. Cl.
USPC ..... Plt./226

(58) Field of Classification Search
USPC ..... Plt./226, 216
See application file for complete search history.

*Primary Examiner* — June Hwu

(74) *Attorney, Agent, or Firm* — Klarquist Sparkman, LLP

(57) ABSTRACT

A *Vitex agnus-castus* plant named 'V0502-33' has medium blue flowers, compound panicles with a greater number of secondary peduncles per panicle; resulting in an unusual stunning floral display.

2 Drawing Sheets

Genus and species: *Vitex agnus-castus*.

Varietal denomination: The new *Vitex agnus-castus* claimed is of the cultivar denominated 'V0502-33'.

BACKGROUND OF THE INVENTION

The present invention relates to a new and distinct cultivar of *Vitex agnus-castus* hereinafter referred to as 'V0502-33'.

Pedigree and history: 'V0502-33' originated from a cross of *Vitex agnus-castus* 'Shoal Creek' (unpatented) and *Vitex rotundifolia* (unpatented) which were caged together with honeybees as pollinators in the summer of 2005 under the direction of David Knauft. Seeds were collected from the female parent 'Shoal Creek', and may have resulted from self-pollination or crosses with *Vitex rotundifolia*. These seeds were sown, and the seedlings were grown in a cultivated area in the spring and summer of 2006. Nineteen plants were selected based on desirable horticultural qualities, and were propagated in Watkinsville, Ga. via stem cuttings in August 2006. In April 2007, the resulting propagated plants in the form of liners were transplanted into containers or the field at a location in Watkinsville, Ga. Based on container and field performance, a plant identified as 'V0502-33' was selected. This 'V0502-33' selection is most likely the result of a self-pollination of 'Shoal Creek'; it is fertile and has no apparent characteristics of *V. rotundifolia*. Stem cuttings were made from this 'V0502-33' plant, and distributed to Carol Robacker, who took over this breeding program in 2009. Plants reproduced from these stem cuttings were planted in a replicated field plot (three reps, randomized block design) in Griffin, Ga. (USDA zone 8a) in the fall of 2009.

'V0502-33' plants have been evaluated for four years at this site. Height and width data have been collected annually. Cold damage was assessed each spring. Mean panicle length and number of panicles per compound panicle were counted each summer. First bloom and re-bloom dates were noted each year. Data was collected on leaf yellowing, leaf drop, thinning, and leaf spot in July, August and September of each year. In addition, two asexually propagated (by cuttings) replicates were also planted in Blairsville, Ga., in spring 2011, to assess performance in this colder environment (USDA zone 7a). In March of 2011, rooted liners of this new plant were shipped to Bonsall, Calif. for evaluation.

*Vitex agnus-castus* is a deciduous shrub or small tree used in landscapes. This drought tolerant plant may be grown in cold hardiness zones 6 through 9. During cold winters in zone 6, it may die back to the ground, but will likely re-grow from the roots and produce a flowering shrub during the following summer, as flower buds are formed on new growth. Late spring freezes in zone 7 may also cause cold damage and dieback, but the plants recover and bloom during the summer. The new plant is intended to be distributed for landscape use in the U.S. and perhaps in other countries.

SUMMARY OF THE INVENTION

'V0502-33' has been grown in an irrigated field plot in Griffin, Ga. and in a non-irrigated plot in Blairsville, Ga. Plants have been fertilized annually in the spring.

The following characteristics have been consistently observed in the original plant of this new variety and in asexually propagated progeny grown from stem cuttings and, to the best knowledge of the inventors, their combination forms the unique characteristics of 'V0502-33' as a new and distinct cultivar. Asexual propagation by cuttings has proven that these characteristics are firmly fixed in succeeding asexually propagated generations.

1. Flower color (medium blue rather than dark blue or purple).

2. Compound panicles with greater number of secondary peduncles per panicle.
3. Unusual and stunning floral display.

Comparison: 'V0502-33' is a unique blue-flowered *Vitex*, as compared to the industry standards 'Shoal Creek' and 'Abbeville Blue' (unpatented). All of the compared plants were propagated from shoot cuttings, rooted and grown in one-gallon containers, before being planted into the field. 'V0502-33' was planted into a field plot in Griffin, Ga. in June 2009 (three reps) and in Blairsville, Ga. in June 2011 (two reps). 'Shoal Creek' and 'Abbeville Blue' were planted into the Griffin, Ga. field plot in June 2010 (one plant each), and 'Abbeville Blue' was planted in Blairsville, Ga. in June 2011. Data in the tables are from plants grown in the Griffin, Ga. field plot. Data given are averages of measurements made on three plants of 'V0502-33' and one plant each of 'Shoal Creek' and 'Abbeville Blue'.

Height and width were measured annually. Both 'Shoal Creek' and 'Abbeville Blue' are somewhat smaller than 'V0502-33' (Table 1). In two out of three years, selection 'V0502-33' began blooming one week later than 'Shoal Creek' and 'Abbeville Blue' (Table 2). Repeat blooming later in the season was similar in 2011 and 2012 for all three genotypes, but in 2013 'V0502-33' had greater repeat blooming than the standard cultivars (Table 3). Flowering is very heavy on 'V0502-33' (FIG. 1). Panicles on 'V0502-33' are shorter and have a slightly smaller diameter than those of either 'Shoal Creek' or 'Abbeville Blue'. 'V0502-33' has a greater number of secondary peduncles per panicle than these two comparison cultivars (Table 4), creating an attractive candelabra appearance (FIGS. 1 and 2).

Very minor cold damage was observed on 'V0502-33' from late spring freezes in Griffin, Ga. (zone 8a) in 2010 and 2011, but no damage occurred in 2012 or 2013. In Blairsville, Ga. (zone 7a), all of the *Vitex* in our field plot lost all of the newly emerged foliage in April 2012. By May, both 'V0502-33' and 'Abbeville Blue' had mostly recovered, though both had some dead branches. By mid-summer, no evidence of the freeze damage was seen, and both bloomed in July. No cold damage occurred in 2013.

*Vitex rotundifolia* has a sprawling growth habit that produces runners that root regularly at nodes. It may grow to 1.5 in tall, though is generally shorter, and will reach over 10 m wide. 'V0502-33' is a small tree that grows upright, reaching 4 m height and 4 m width. The foliage on *V. rotundifolia* is mostly simple, while on 'V0502-33' the foliage is compound, palmate with mostly 7 leaflets. Inflorescences on *V. rotundifolia* are 3 to 7 cm in length, while on 'V0502-33' they are 15 cm in length.

TABLE 1

Height and width (cm) of *Vitex* 'V0502-33', 'Shoal Creek' and 'Abbeville Blue' one, two and three years after planting in a field plot in Griffin, Georgia. Data for 'V0502-33' is the average of three plants and 'Shoal Creek' and 'Abbeville Blue' are each based on one plant.

| Entry | Year 1 | Year 2 | Year 3 |
|---|---|---|---|
| 'V0502-33' | 194 H × 258 W | 298 H × 394 W | 371 H × 360 W |
| 'Shoal Creek' | 172 H × 303 W | 295 H × 367 W | 345 H × 385 W |
| 'Abbeville Blue' | 168 H × 228 W | 255 H × 308 W | 270 H × 372 W |

TABLE 2

First bloom dates of V0502-33, 'Shoal Creek' and 'Abbeville Blue' grown in Griffin, Georgia.

| Entry | First bloom 2011 | First bloom 2012 | First bloom 2013 |
|---|---|---|---|
| 'V0502-33' | 5-30 | 5-21 | 6-17 |
| 'Shoal Creek' | 5-30 | 5-14 | 6-10 |
| 'Abbeville Blue' | 5-30 | 5-14 | 6-10 |

TABLE 3

Repeat flowering in July, August, September and October in 2011, 2012, and 2013.

| Entry | Year | July | August | September | October |
|---|---|---|---|---|---|
| 'V0502-33' | 2011 | 0* | 1.2 | 2.7 | 0.8 |
| | 2012 | 0 | 1.5 | 4.0 | 2.2 |
| | 2013 | 0.7 | 0.2 | 3.0 | 2.2 |
| 'Shoal Creek' | 2011 | 2 | 1 | 3 | 1 |
| | 2012 | 0 | 1 | 4 | 2.5 |
| | 2013 | 0 | 0 | 1 | 0.5 |
| 'Abbeville Blue' | 2011 | 1 | 0 | 2 | 1 |
| | 2012 | 0 | 1 | 3 | 3 |
| | 2013 | 0 | 0 | 0 | 0.5 |

*Repeat flowering was rated using the following scale: 0 = no flowering; 1 = 10% full bloom; 2 = 20 to 30% full bloom; 3 = 40 to 50% full bloom; 4 = at least 60% full bloom.

TABLE 4

Panicle length, diameter and number of secondary peduncles per panicle, averaged over 2011, 2012, and 2013. Measurements were made on four typical or average-sized panicles per plant per year.

| Entry | Mean panicle length (cm) | Mean panicle diameter (cm) | Number of secondary peduncles |
|---|---|---|---|
| 'V0502-33' | 15.7 | 3.2 | Four to seven |
| 'Shoal Creek' | 24.1 | 3.8 | Three to six |
| 'Abbeville Blue' | 22.9 | 3.8 | Two to six |

BRIEF DESCRIPTION OF THE PHOTOGRAPHS

The accompanying colored photographic illustrations show the overall appearance and distinct characteristics of the new cultivar of *Vitex agnus-castus*. The colors in the photographs are as close as possible with the photographic and printing technology utilized.

DETAILED BOTANICAL DESCRIPTION

Figure 1:
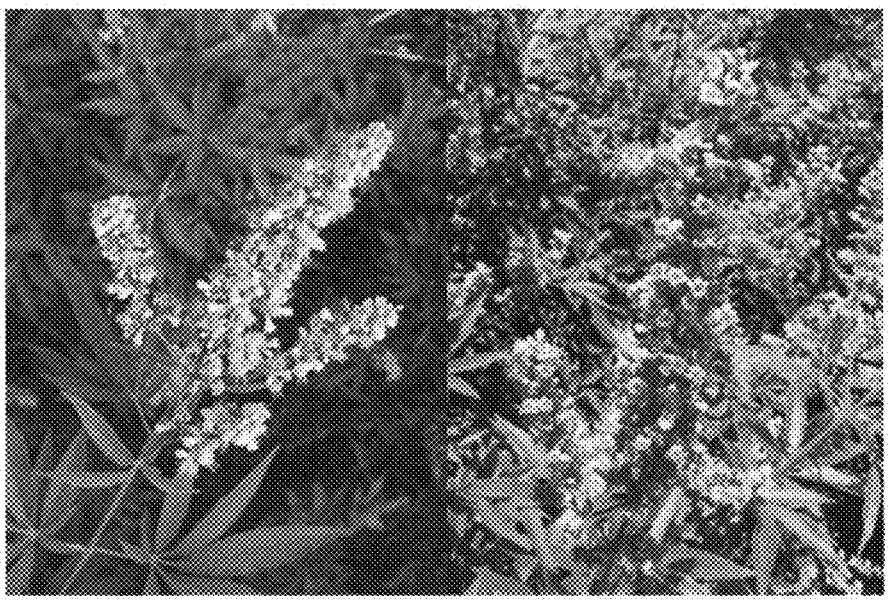
FIG. 1 is a photograph of panicles of cultivars 'Shoal Creek' and 'Abbeville Blue' (top) and 'V0502-33' (bottom). 'V0502-33' has a greater number of sub-panicles than the standard cultivars.
Figure 1:
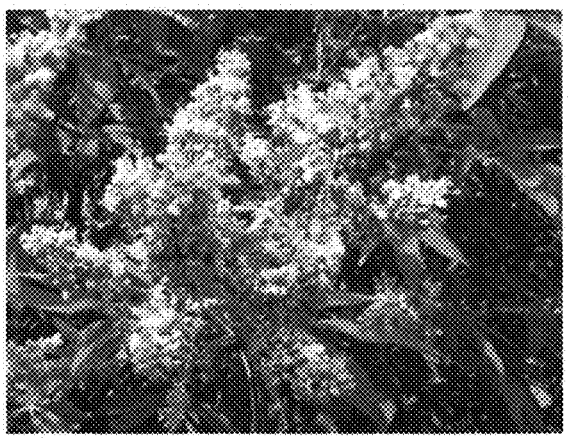
Figure 2:
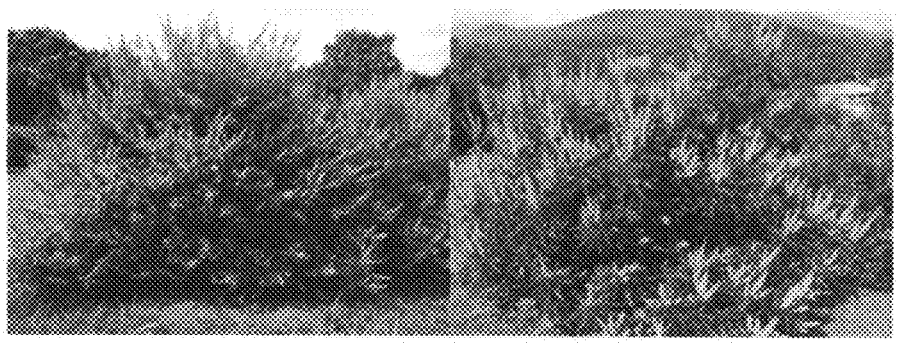
FIG. 2 is a photograph of peak bloom of cultivars 'Shoal Creek' and 'Abbeville Blue' (top) and 'V0502-33' (bottom). There are different panicle forms. 'Shoal Creek' and 'Abbeville Blue' flowers are darker in color than 'V0502-33', which has lighter blue flowers.
Figure 2:
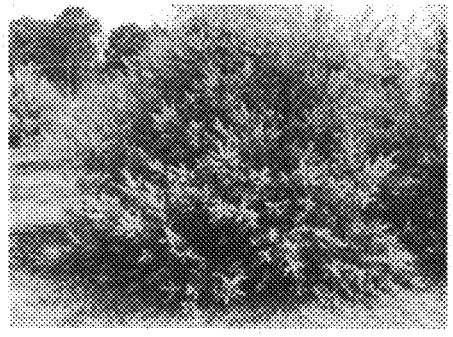

The following is a detailed description of the *Vitex agnus-castus* cultivar named 'V0502-33'. Data was collected in Griffin, Ga. from three year old plants grown from cuttings and growing outdoors. 'V0502-33' has not been tested under all possible conditions hence, phenotypic differences may be observed with variations in environmental conditions without any variance in genotype.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society (R.H.S.), London, England. This description is from observations of typical three year old plants growing in Griffin, Ga.

Parentage:

*Female parent*.—'Shoal Creek'.

*Male parent*.—'Shoal Creek' or *Vitex rotundifolia*, most likely 'Shoal Creek'.

Habit: Open, spreading, upright.

Size (h×w): 394 cm×409 cm.

Texture: Medium coarse.

Stems:

*First year*.—Color — Grey-Brown N199A. Diameter — 4 to 5 mm. Pubescence — covered in minute hairs. Exfoliation — none. Shape (angled, terete, round, etc.) — round. Pith — Type — solid. Diameter — 3 mm. Color (RHS) — White N155D. Odor (of bruised stem) — strong, spicy, acrid. Lenticels — none observed. Internode length — 7.5 cm.

*Second year*.—Color (RHS) — Grey-Green 197A. Diameter — 7.5 mm. Exfoliation — none.

Vegetative buds:

*Arrangement*.—Opposite.

*Type*.—Valvate.

*Size* (*l*×*w*).—1 mm×2 mm.

*Scale number*.—2.

*Scale color*.—Greyed-Orange 177D.

*Position/disposition*.—45°.

*Number at node*.—2, one on each side.

*Pubescence*.—Scattered short hairs.

*Shape*.—Rounded dome.

Leaf scar:

*Shape*.—Cup shaped.

*Vascular bundle traces*.—3, horizontal and oval.

*Pubescence*.—Dense minute hairs around perimeter.

*Position of bud* (*on leaf scar*).—Just above the leaf scar.

*Color differentiation*.—144A.

*Size* (*h*×*w*).—3×3 mm.

Trunk or large stems:

*Colors*.—Mix of Greyed-White 156A and Greyed-Brown 199D.

*Size stem exfoliation begins on*.—Approx. 5 cm.

*Diameter*.—3 to 5.0 cm.

*Texture*.—Smooth younger stems, striations start at approx. 3 cm, cracking by 5.0 cm.

Leaf:

*Color through seasons*.—Emerging — mid April. Upper: Yellow-Green 144A. Lower: Greyed-Green 191B. Summer — mid July. Upper: Green 137A. Lower: Greyed-Green 191B. Fall — September. Upper: Yellowed-Green 147A. Lower: Greyed-Green 191B.

*Mature size* (*l*×*w*).—15 cm×18 cm.

*Apex*.—Acuminate.

*Base*.—Acuminate.

*Margin*.—Entire.

*Shape*.—Palmate, mostly 7 leaflets. Lobes — none. Sinuses — none.

*Vein color*.—Yellow-Green 145C.

*Pubescence*.—Upper surface has many scattered hairs, with more along the midvein , slightly glandular surface. Lower leaf is more densely hairy and has a very glandular surface.

*Arrangement on stem*.—Opposite.

*Venation*.—Pinnate.

*Texture*.—Thickness — 0.3 mm. Degree of waxiness of surfaces — slightly waxy but dull on upper surface, completely dull on lower surface.

*Foliage fragrance*.—Mild, spicy.

*Average size of leaflets*.—The leaflets of five leaves that had seven leaflets per leaf were measured. The leaflets are arranged palmately, going from small to medium to large to medium to small. Mean lengths and widths of the seven leaflets are as follows: 34.2 mm long, 6.2 mm wide; 54.4 mm long, 10.8 mm wide; 71.4 mm long, 14.4 mm wide; 78.8 mm long, 16.8 mm wide; 72.2 mm long, 13.4 mm wide; 37.2 mm long, 9.4 mm wide; 32.5 mm long, 5.0 mm wide.

Petiole:

*Length*.—5.5 cm.

*Shape*.—Round.

*Color*.—Upper Yellow-Green 148C, lower Yellow-Green 145B.

*Pubescence*.—Densely covered in minute curved hairs.

*Diameter*.—1.8 mm.

Flower buds:

*Size* (*l*×*w*).—7 mm×3 mm.

*Color*.—Violet-Blue 91B.

*Shape*.—Teardrop.

*Pubescence*.—Glandular surface, dense hairs laying flat.

*Time of full maturity*.—Early summer.

*Time range for showiness*.—Early to mid-June through September.

Flower:

*Inflorescence*.—Type — elongated panicle, compound. Size 15 cm long×3 cm wide (largest subpanicle in the panicle); individual floret — 8 mm long×6 mm wide. Color — At emergence: Violet-Blue 92A. Full bloom: Violet-Blue 92A. Fading: Violet-Blue 91A. Peduncle — Color: Greyed-Green 193A. Pubescence: tomentose, sparsely glandular. Number of individual flowers per inflorescence — 244-562. Fragrance — mild, sweet, floral.

*Petals*.—Size — 8 mm×6 mm. Shape — zygomorphic, gamopetalous, bilabiate. Apex — 5 lobes rounded and slightly curled. Base — funnel. Margin — slightly curled. Pubescence — mostly glabrous, scattered glandular with thick tuft of hairs inside base and many short, flat, glandular hairs outside; a few longer hairs on anterior petal. Texture — mostly smooth. Color at peak of bloom — Upper surface: Violet-Blue 92A. Lower surface: Violet-Blue 92C. Pedicels: Color — Greyed-Green 193A. Pubescence — many short hairs. Length — 1-2 mm.

*Sepals*.—Size (l×w) — 4 mm×2 mm. Shape — united, slightly lobed. Apex — slightly lobed. Base — united, short tubular. Margin — smooth. Pubescence — glandular, tomentose — short hairs. Texture — hoary. Color at peak of bloom Upper surface — Greyed-Green 193A and Greyed-Purple N187B. Lower surfaces — Yellow-Green 144C with Violet-Blue 93C.

*Male reproductive structures*.—Number — 4. Anther — Size (l×w) — 1.5 mm×0.5 mm. Color — Violet-Blue 90A. Filament Size (l×w) — 6 mm×0.5 mm. Color — Purple 76B. Pollen color — White 155C. Pubescence — thick tuft at base.

*Female reproductive structures*.—Pistil — Shape: tubular, bifid. Size (l×w): 7 mm×0.5 mm. Position: superior. Color: Violet 84B. Pubescence: thickly tufted hairs at base. Stigma — Shape: round, bifid. Color: White 155C. Pubescence: none. Style — Length: 6 mm. Shape: tubular, forked at stigma (bifid). Color: Violet 84A. Pubescence: none, but tufted at base. Ovary — Shape: round. Number: 1. Pubescence: scattered short hairs, numerous glands present on surface.

Fruit:

*Type*.—Drupe-like.

*Size* (*l*×*w*).—3.5 mm×2.5 mm.

*Colors during ripening*.—Early — Yellow-Green 151C. Mid — Greyed-Orange 166B. Late — Brown 200A.

*Shape*.—Globular.

*Number per infructescence*.—1.

*Pubescence*.—Few scattered hairs.

*Number of carpels*.—2.

*Persistence*.—Mid to late summer through fall into winter.

Seed:

*Shape*.—Globular.

*Size*.—3.5 mm×2.5 mm, oval.

*Color*.—Brown 200A when fully ripe.

*Number per locule per ovary per fruit*.—1.

*Pubescence*.—Scattered minute hairs.

Disease and pest resistance: Not observed to date.

Hardiness: The new plant has been successfully grown in USDA hardiness zone 8a. The new plant has also been successfully grown in USDA hardiness zone 6b, though some die back from cold has been observed in plants grown in this hardiness zone.

What is claimed is:

1. A new and distinct cultivar of the *Vitex agnus-castus* plant named 'V0502-33' substantially as illustrated and described herein.

* * * * *

'Shoal Creek' 'Abbeville Blue'

'V0502-33'

'Shoal Creek' 'Abbeville Blue'

'V0502-33'